(12) United States Patent
Kumar et al.

(10) Patent No.: US 12,046,623 B2
(45) Date of Patent: Jul. 23, 2024

(54) COMPOUND SEMICONDUCTOR X-RAY DETECTOR TILES AND METHOD OF DICING THEREOF

(71) Applicant: REDLEN TECHNOLOGIES, INC., Saanichton (CA)

(72) Inventors: Francis Joseph Kumar, Victoria (CA); Michael K. Jackson, Victoria (CA); Pramodha Marthandam, Victoria (CA)

(73) Assignee: REDLEN TECHNOLOGIES, INC., Saanichton (CA)

( * ) Notice: Subject to any disclaimer, the term of this patent is extended or adjusted under 35 U.S.C. 154(b) by 411 days.

(21) Appl. No.: 17/395,794

(22) Filed: Aug. 6, 2021

(65) Prior Publication Data

US 2022/0045118 A1    Feb. 10, 2022

Related U.S. Application Data

(60) Provisional application No. 63/062,625, filed on Aug. 7, 2020.

(51) Int. Cl.
| | |
|---|---|
| *H01L 31/00* | (2006.01) |
| *A61B 6/03* | (2006.01) |
| *H01L 27/146* | (2006.01) |

(52) U.S. Cl.
CPC ........ *H01L 27/14659* (2013.01); *A61B 6/032* (2013.01); *H01L 27/14696* (2013.01); *H01L 27/14698* (2013.01)

(58) Field of Classification Search
CPC ........... B82Y 20/00; B82Y 30/00; C30B 1/00; C30B 3/00
See application file for complete search history.

(56) References Cited

U.S. PATENT DOCUMENTS

| | | | |
|---|---|---|---|
| 5,182,233 A | 1/1993 | Inoue | |
| 6,034,373 A | 3/2000 | Sharhar et al. | |
| 6,928,144 B2 | 8/2005 | Li et al. | |
| 7,432,577 B1 * | 10/2008 | Weiss | H01L 31/108 257/E31.026 |
| 9,847,369 B2 | 12/2017 | El-Hanany et al. | |
| 10,276,627 B2 | 4/2019 | El-Hanany et al. | |
| 11,105,938 B2 | 8/2021 | Harris et al. | |

(Continued)

OTHER PUBLICATIONS

Bosma, M. et al., "The influence of edge effects on the detection properties of cadmium telluride," 2011 IEEE Nuclear Science Symposium Conference Record, 2011, pp. 4812-4817, doi: 10.1109/NSSMIC.2011.6154720.

(Continued)

*Primary Examiner* — Don K Wong
(74) *Attorney, Agent, or Firm* — THE MARBURY LAW GROUP PLLC

(57) ABSTRACT

A radiation detector tile includes a single crystal compound semiconductor tile having a zinc blende crystal structure, a (111) plane first major (i.e. prominent) surface and four side surfaces which are rotated by an angle of 13° to 17° to a {110} family of planes. The tile may be formed by dicing a (111) oriented wafer at directions which are rotated by an angle of 13° to 17° from <110> in-plane slipping directions to reduce or eliminate the side surface chipping and sub surface dislocation defects.

8 Claims, 9 Drawing Sheets

(56) References Cited

U.S. PATENT DOCUMENTS

| | | |
|---|---|---|
| 2016/0133776 A1 | 5/2016 | Kishi et al. |
| 2016/0240584 A1 | 8/2016 | El-Hanany et al. |
| 2018/0033822 A1 | 2/2018 | El-Hanany et al. |
| 2018/0329079 A1 | 11/2018 | Lu et al. |
| 2020/0393576 A1 | 12/2020 | Harris et al. |

OTHER PUBLICATIONS

Crocco, J. et al., "Study of the Effects of Edge Morphology on Detector Performance by Leakage Current and Cathodoluminescence," in IEEE Transactions on Nuclear Science, vol. 58, No. 4, pp. 1935-1941, Aug. 2011, doi: 10.1109/TNS.2011.2157703.

Duarte, D. "Edge effects in a small pixel CdTe for X-ray imaging," Journal of Instrumentation, vol. 8, No. 10, pp. P10018, (2013) DOI:10.1088/1748-0221/8/10/P10018.

Nakagawa, K. et al., "Observation of dislocations in cadmium telluride by cathodoluminescence microscopy," Appl. Phys. Lett. Vol. 34, pp. 574 (1979); https://doi.org/10.1063/1.90871.

Nakagawa, K. et al., "Improvement of the CdTe diode detectors using a guard-ring electrode," in IEEE Transactions on Nuclear Science, vol. 51, No. 4, pp. 1881-1885, Aug. 2004, doi: 10.1109/TNS.2004.832684.

Afshar, A. et al., "Radiation Sensor Dies Having Visual Identifiers and Methods of Fabricating Thereof," U.S. Appl. No. 17/931,397, filed Sep. 12, 2022.

\* cited by examiner

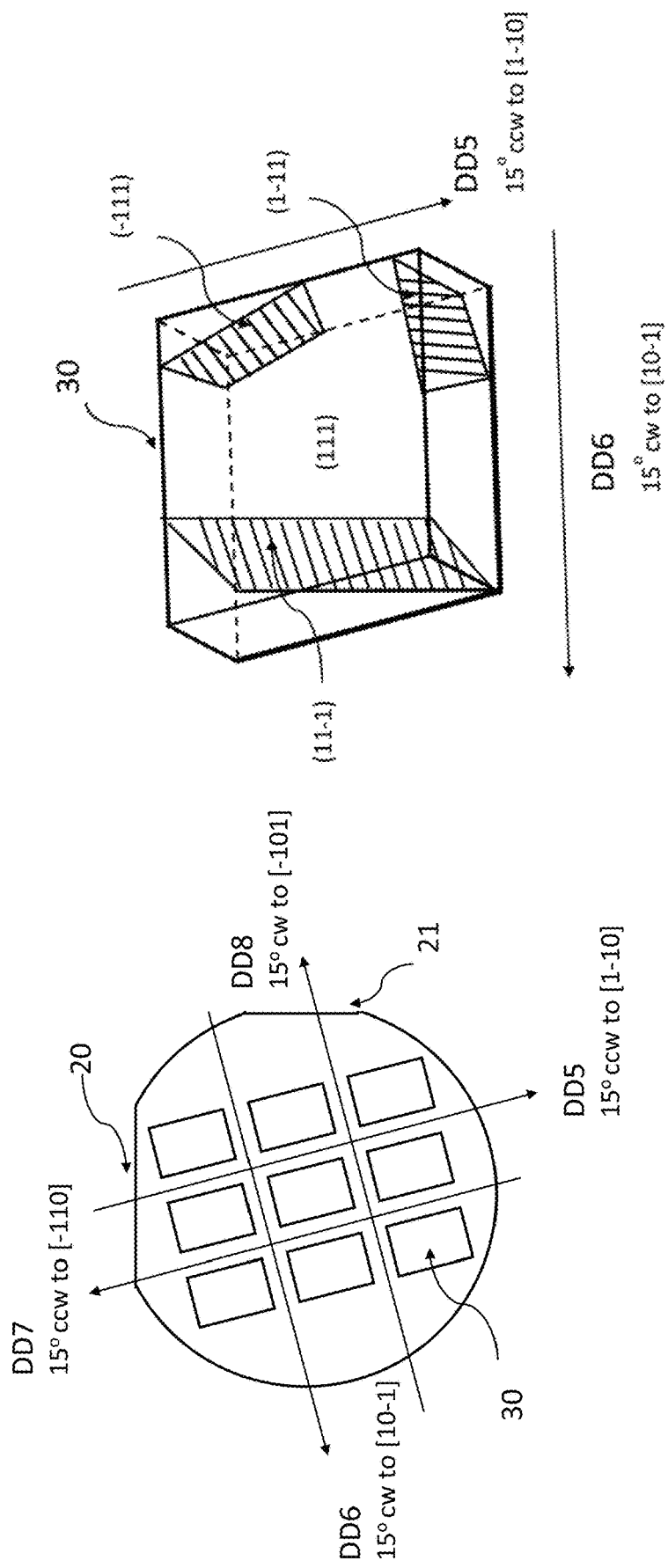

COMPOUND SEMICONDUCTOR X-RAY DETECTOR TILES AND METHOD OF DICING THEREOF

FIELD

The invention relates to compound semiconductor radiation detectors, in particular to X-ray detector tiles, and further to a method of dicing the tiles from a compound semiconductor wafer.

BACKGROUND

Miller index notation is used to specify the crystal planes and orientation directions. As used herein, a crystal plane is represented as (h k l), and the family of eight equivalent planes of a cubic lattice (h k l), (−h k l), (h −k l), (h k −l), (−h−k l), (−h k−l), (h−k−l) & (−h−k−l) are represented by {h k l}. Furthermore, in a cubic lattice, the direction perpendicular to (h k l) plane is represented by [h k l] and the family of equivalent directions is represented by <h k l>.

A compound semiconductor wafer may be formed by slicing a single crystal boule along any of the low index planes such as {100}, {110} and {111}. The wafer slicing orientation is based on factors such as direction of the single crystal boule growth, the electrical properties required for the semiconductor device to be fabricated from the wafer, and optimum use of the single crystal boule to increase the production yield. For instance in the case of a II-VI compound semiconductor having a zinc blende crystal structure formed by two interpenetrating FCC lattices of II group and VI group atoms, the {110} planes are nonpolar while the {100} and {111} planes have a polar attribute dependent on whether the surface is terminated with a II group atom or a with a VI group atom. In the case of a cadmium telluride ("CdTe") semiconductor, the {111} plane surface which has a Cd termination is by convention the (111) surface while the opposite (−1−1−1) surface has a Te termination. Similar nomenclature is used for iso-valent alloys of CdTe, such as cadmium zinc telluride ("CZT") compound semiconductors having a formula $Cd_{(1-x)}Zn_xTe$, where x is greater than zero and less than one, or cadmium selenide telluride or cadmium zinc selenide telluride. For CdTe or its iso-valent based alloy radiation detectors, such as X-ray detectors, the pixelated anode metallization of the X-ray detector may be formed on the (111) surface while the cathode metallization may be formed on the (−1−1−1) surface. Such a bias voltage configuration works similar to a reverse biased p-n junction diode and greatly restricts the leakage current passing through the detector.

SUMMARY

In one embodiment, a radiation detector tile includes a single crystal compound semiconductor tile having a zinc blende crystal structure, a (111) plane first major surface and four side surfaces which are rotated by an angle of 13° to 17° to a {110} family of planes.

In another embodiment, a dicing method includes providing a single-crystal II-VI compound semiconductor material having a zinc blende crystal structure and having two surfaces which comprise (111) and (−1−1−1) planes, dicing the single-crystal II-VI compound semiconductor material along first dicing directions in a direction rotated by an angle of 13° to 17° to a {110} family of planes, dicing the single-crystal II-VI compound semiconductor material along second dicing directions which are opposite to the first dicing directions, dicing the single-crystal II-VI compound semiconductor material along third dicing directions which are orthogonal to the first and the second dicing directions, and dicing the single-crystal II-VI compound semiconductor material along fourth dicing directions which are opposite to the third dicing directions.

In another embodiment, a dicing method includes providing a single-crystal II-VI compound semiconductor wafer having a zinc blende crystal structure, dicing the single-crystal II-VI compound semiconductor wafer along first dicing directions, dicing the single-crystal II-VI compound semiconductor wafer along second dicing directions which are opposite to the first dicing directions, dicing the single-crystal II-VI compound semiconductor wafer along third dicing directions which are orthogonal to the first and the second dicing directions, and dicing the single-crystal II-VI compound semiconductor wafer along fourth dicing directions which are opposite to the third dicing directions to form a plurality of active detector tiles. The II-VI compound semiconductor wafer is diced in both the first and the second directions between two active detector tiles of a first pair of adjacent active detector tiles to leave a first dummy tile between the two active detector tiles of the first pair of adjacent active detector tiles. The first dummy tile has a smaller area than each of the two active detector tiles.

BRIEF DESCRIPTION OF THE DRAWINGS

The embodiments of the present invention can be better understood and the advantages can be appreciated when considered concurrently with the drawings. Identical indicator numbers refer to the same or similar parts throughout the several illustrations.

FIG. 5 is top view of a II-VI semiconductor wafer illustrating the dicing schematic rotated 15° to the orientation flat according to another embodiment of the present disclosure.

FIG. 6 is a perspective view of a II-VI semiconductor tile showing orientation of the slip planes in the detector tile with edges offset 15° to the orientation flat according to an embodiment of the present disclosure.

DETAILED DESCRIPTION

Figure 1B:
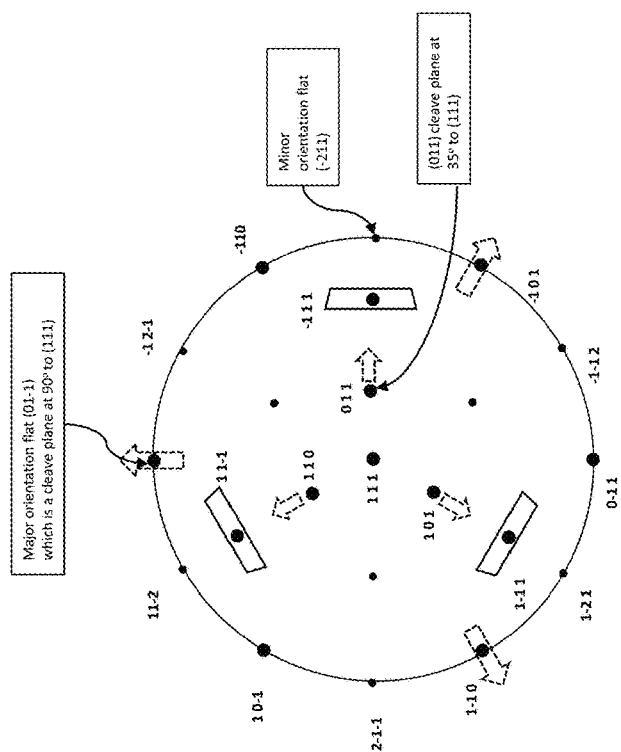
FIGS. 1A and 1B are schematic diagrams of the stereographic projection of a (111) face centered cubic (FCC) plane showing slip directions and slip planes.

When the detector tiles are formed from a {111} oriented II-VI wafer (i.e., which has major (−1−1−1) and (111) surfaces), in general, the wafer is diced along a {110} cleavage plane because the crystal may split easily along this plane. However due to the specific crystallographic nature of the (111) oriented wafer plane, the orthogonal cut occurs in a direction perpendicular to the cleavage plane and has no such cleaving benefits. Furthermore, when diced in a direction which is not perfectly aligned in a cleavage direction, a lot of cutting damage such as chipping and dislocations in the subsurface of the tile may occur.

Anode pixels on the edges of the detector are sensitive to defects created at the crystal (e.g., tile) edge during dicing. These defects create increased surface currents that flow around the corners and edges of the detector tile and increase charge generation, which can cause premature reverse breakdown in the detector tiles which are configured as Schottky diodes, as well as excess currents at operating voltages. Defects arising from cutting may also create high density of traps with long de-trapping time and result in ballistic deficit and reduction in charge collection efficiency of edge pixels.

The present inventors realized that when a (111) oriented wafer having a cubic zinc blende crystal structure (e.g., a compound semiconductor wafer, such as a II-VI wafer, such as a CdTe or CZT wafer) is diced, the slip systems associated with the in-plane slip directions such as [1−10], [01−1] and [−101] create mostly slip dislocations. The slip systems associated with the out of plane slip directions such as [101], [110] and [011] create mostly cracks and chips.

It is industry practice to form orientation flats in the wafer during the processing. The selection of the orientation of the flats is a matter of choice among several possible crystallographic directions to serve several purposes, such as surface polarity identification, and may be done by an X-ray diffraction method. When dicing is done in the directions perpendicular to the orientation flat which is oriented parallel to any one of the three in-plane slipping directions (e.g., <110> directions) of the wafer's (111) surface, which are also the cleavage planes normal to the surface, both the in-plane and out of plane slip systems are active and cause the tile edges to chip heavily and to create dislocations in the sub surfaces. More specifically, such damage is observed only on one side of the dicing line and is absent on the other side. Furthermore, if the good (i.e., undamaged) side appears on the left hand side of the dicing line in one direction, then the good side appears on the right hand side of the dice on a 180° reversal. Thus, the side of the tile on which the dicing damage is absent remains the same irrespective of the 180° reversal of the dicing direction. In other words there is always one bad (i.e., damaged) side of the tile. However, when dicing is done in directions (e.g., <112> directions) parallel to the major orientation flat, the beneficial nature of the cleavage plane can be obtained.

The present inventors further realized that when dicing is done at an angle between 13° and 17°, such as between 14° and 16°, such as 15° with respect to the major orientation flat, the activity of the out of plane slip systems are eliminated on one side of the cut and are suppressed on the other side of the cut. Furthermore, a left-right anisotropy of the opposing tile edge quality is thus obtained. In some embodiments, by utilizing such anisotropy and by dicing sacrificial tiles in between active detector tiles, it is possible to produce detector tiles having minimal defects on all sides or on two opposing sides, as will be described below with respect to FIGS. 8 and 9 below. Thus, the embodiments of the present disclosure provide a detector tile fabrication process which reduces or limits the potential adverse effects of diced tile side surfaces on the final detector performance.

Figure 1A:
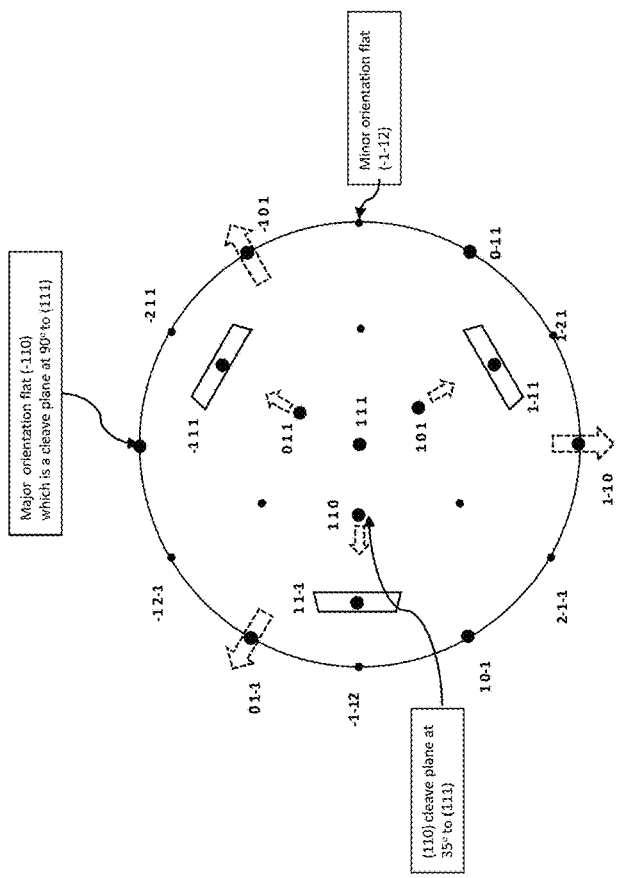

FIG. 1A is the stereographic projection (i.e., the pole figure) for the (111) orientation of a FCC crystal lattice. Two such FCC lattices, one for II group and another for the VI group atoms which are displaced by ¼ of the unit cell dimension along the cell diagonal form the zinc blende crystal structure of a II-VI compound semiconductor, such as CdTe or CZT. FIG. 1A is a projection for a Type I major orientation flat zinc blende wafer having a 35 degree cleave at a side opposite to the (−1−12) minor orientation flat, and a (−110) major orientation flat. FIG. 1B is a projection for the Type II major orientation flat zinc blende wafer having the 35 degree cleave at the same side as the (−211) minor orientation flat and a (01−1) major orientation flat. Thus, the projection in FIG. 1B is rotated clockwise by 60 degrees from the projection in FIG. 1A. All examples described below are for Type I major orientation flat wafers unless specified otherwise. In one embodiment, the major orientation flat may be placed on a zinc blende boule or wafer such that the resulting wafers are Type I major orientation flat wafers. The boule or wafer may be characterized by side cleaving, Everson etching or non-contact resistivity measurement to place the major orientation flat in a position to achieve a Type I major orientation flat wafer. For example, the boule or wafer may be characterized by checking for the three 35° {110} cleavage planes on the periphery or observing the orientation of the dislocation etch pits revealed by chemical etching, to place the major orientation flat in a position to achieve a Type I major orientation flat. In the stereographic projections shown in FIGS. 1A and 1B, the center dot represents the [111] direction, each other dot represents a specific lattice plane, i.e., its plane normal whose tilt angle from [111] direction is delineated by its radial distance from the center. The circle is the 90° boundary. In addition to the dot representation, the three {111} slip planes are provided with trapezoids and the six <110> slip directions are provided with dotted arrows in an effort to elucidate the various slip systems and slip dislocation directions.

The nine slip systems which determine the dislocation generation and chipping during dicing of a wafer with major surfaces (111) and (−1−1−1) are as follows: (11−1) plane slipping in either one of the three directions [1−10], [011] & [101]; (−111) plane slipping in either one of the three directions [01−1], [101] & [110] and (1−11) plane slipping in either one of the three directions [−101], [110] & [011].

Figure 2:
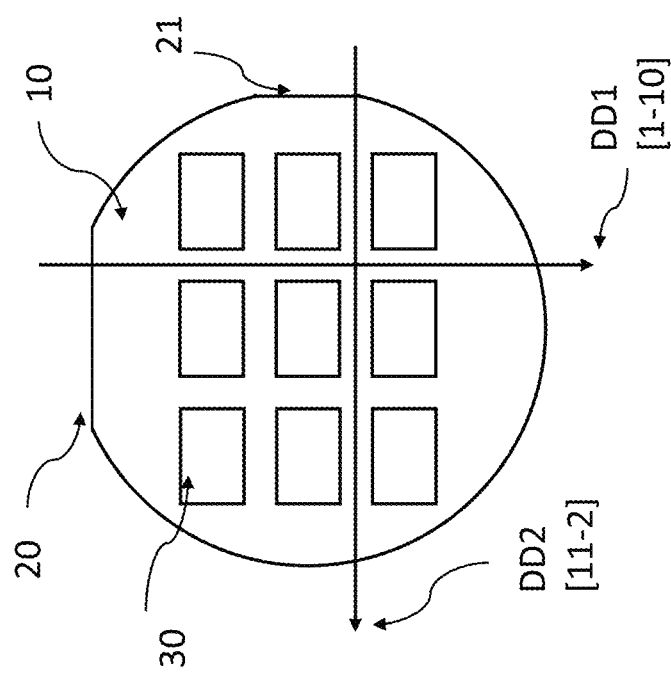
FIG. 2 is top view of a II-VI semiconductor wafer illustrating the comparative example dicing schematic aligned to the orientation flat.

FIG. 2 illustrates the schematic of the CdTe or CZT wafer 10 with (111) plane as the prominent surface and having the major orientation flat 20 in a (−110) plane and the minor orientation flat 21 in a (−1−12) plane according to a comparative example. The orientation flats 20 and 21 serve the purpose of easy recognition of the surface polarity as (111). The orientation flats are formed during the boule surface grinding process using an X-ray diffraction method. After the orientation flats are ground on the periphery of the boule, the boule is sliced into wafers. FIG. 2 further illustrates dicing directions DD1 and DD2 (i.e., [1−10] and [11−2] directions) of the wafer 10 to form detector tiles 30 whose side surfaces are oriented parallel to the (−110) and (11−2) planes.

Figure 3:
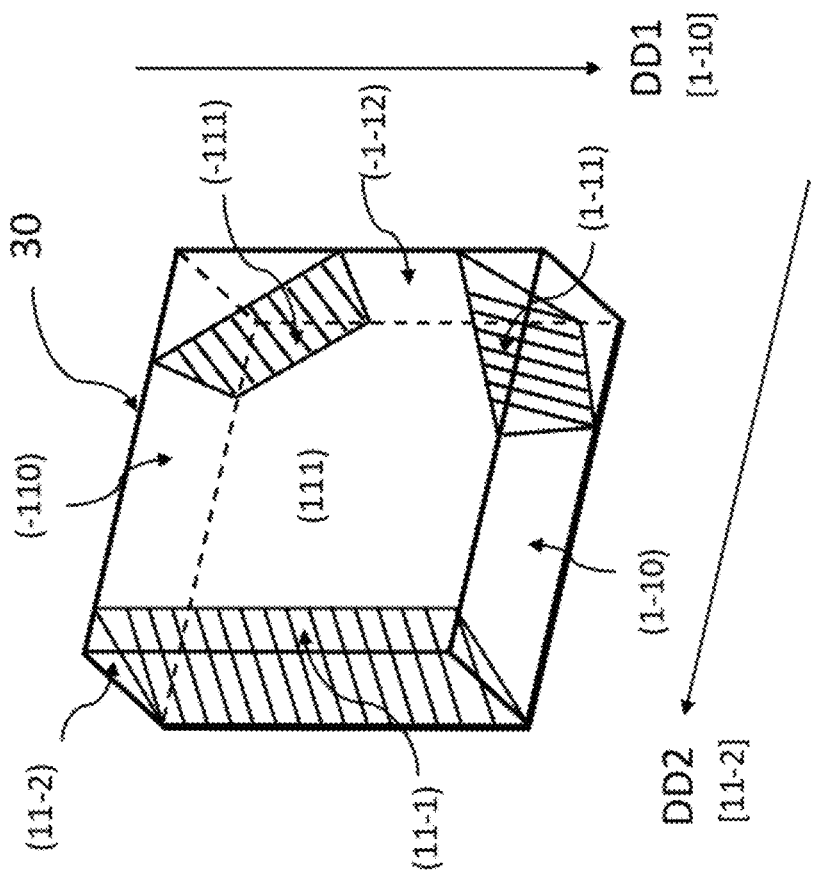
FIG. 3 is a perspective view of a II-VI semiconductor tile showing orientation of the slip planes in the detector tile with edges aligned perfectly to the orientation flat according to a comparative example.

FIG. 3 is a schematic perspective view of a CdTe detector tile 30 according to a comparative example obtained by the dicing the wafer 10 along directions DD1 and DD2. As shown in FIG. 3, the major surface of the detector tile 30 is a (111) plane and the edge planes are (−110), (−1−12), (1−10) and (11−2) planes. Also illustrated in the FIG. 3 are the three slip planes (−111), (1−11) and (11−1) which are mutually oriented with each other and to the (111) wafer plane at 70.5°. FIGS. 1A & 3 also illustrate that the dicing done in the [11−2] direction need not produce the same quality of cut as a parallel cut done in the 180° opposite direction i.e., [−1−12]. This is because of the projection and tilt of the three slip planes to the direction of the cut are not the same.

To further illustrate the intricate nature of the slip systems and slipping directions, a (111) oriented CZT wafer according to the comparative example was scribed on the (111) face using a carbide scribing tip with a tip radius of 125 microns at a 15° angular intervals under constant loading and with the major orientation flat as the initial reference. The scribed wafer was subsequently etched with a Nakagawa etching solution to reveal the dislocation etch pits. The Nakagawa etching solution method is an industry standard for revealing the dislocation etch pits on the (111) surface of CdTe and CZT, as described in Nakagawa et al., Observation of dislocations in cadmium telluride by cathodoluminescence microscopy, Appl. Phys. Lett. 34 (9) (1979) 574-575, incorporated herein by reference in its entirety.

Figure 4A:
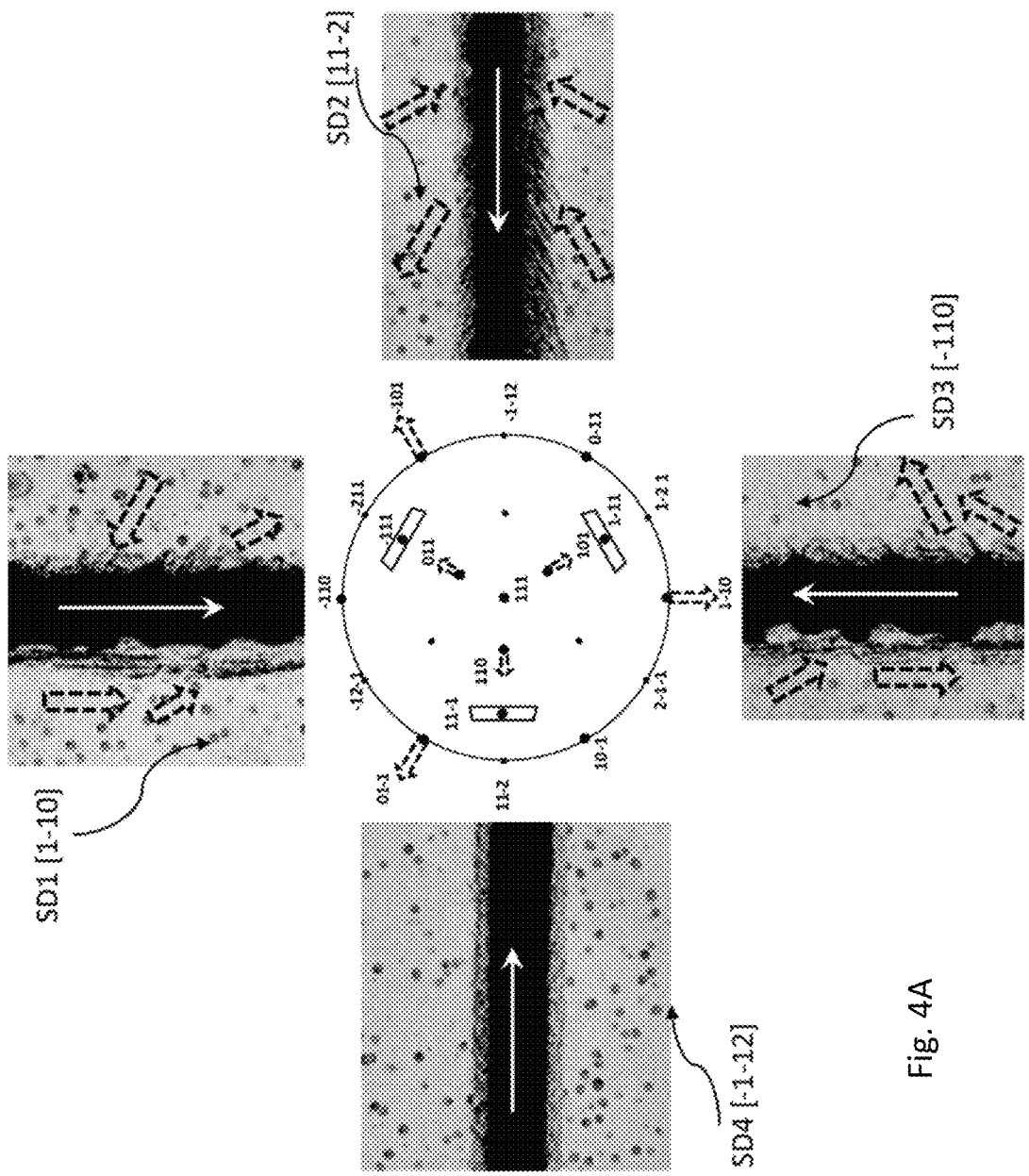
FIG. 4A shows micrographs of slip systems active during dicing of a (111) CZT wafer in directions parallel and perpendicular to the orientation flat relative to the schematic diagram of the stereographic projection shown in FIG. 1A. The slip systems are revealed by scribing in the illustrated directions and the dislocation pits highlighted by a Nakagawa etching solution.

The optical micrographs in the FIG. 4A illustrate the side wall chipping and sub surface dislocation etch pits highlighted by the wet chemical etching of the scribed areas when scribed in the four directions SD1 to SD4 which are the [1−10], [11−2], [−110] and [−1−12] directions. The slip systems which are active in each of these scribing directions are marked with the dotted black colored arrows coinciding with the etch pits and chipping patterns. The white colored arrow in the middle of the scribed area indicates the direction of the scribe. The (111) pole figure is also presented together with the optical micrographs for ready visualization and correlation angles of the black arrows to the respective slip planes and slipping directions.

For scribing in the [1−10] direction (SD1), the active slip systems are (11−1)/[1−10] at 0° & (11−1)/[101] at −30° to the right and (−111)/[101] at −30° & (−111)/[0−11] at 60° to the left of dicing direction. Here, (11−1)/[1−10] and (−111)/[0−11] are in plane slip systems; (11−1)/[101] (−111)/[101] are out of plane slip systems for the (111) wafer. Furthermore, dicing experiments and device level testing revealed that, for scribing direction SD1, the high quality edges are obtained on the right hand side of the dicing direction where the slip dislocations run parallel to the dicing direction. In contrast, the left hand side of the dicing direction is of poor quality where the slip dislocations run deeper across the edge into the tile cross section due to the 60° angle to the dicing direction.

For scribing in the [11−2] direction (SD2), the active slip systems are (−111)/[01−1] at 30° & (−111)/[101] at −120° to the right and (1−11)/[−101] at 150° & (1−11)/[011] at 120° to the left of the scribing direction. Here, (−111)/[01−1] and (1−11)/[−101] are in plane slip systems; (−111)/[101] and (1−11)/[011] are out of plane slip systems for the (111) wafer.

For scribing in the [−110] direction (SD3), the active slip systems are (11−1)/[1−10] at 180° & (11−1)/[101] at 150° to the left and (1−11)/[011] at 30° & (1−11)/[−101] at 60° to the right of scribing direction. Here, (11−1)/[1−10] and (1−11)/[−101] are in plane slip systems; (11−1)/[101] and (1−11)/[011] are out of plane slip systems for the (111) wafer. Furthermore, dicing experiments and device level testing revealed that, for dicing direction SD3, the high quality edges are obtained on the left hand side of the dicing direction where the slip dislocations run parallel to the dicing direction. In contrast, the right hand side of the dicing direction is of poor quality where the slip dislocations run deeper across the edge into the tile cross section due to the 60° angle to the dicing direction. Thus, irrespective of the reversal in the dicing direction, the good and bad sides of the diced tile will remain the same, in view of dicing in the two antiparallel dicing directions SD1 and SD3 described above.

For scribing in the [−1−12] direction (SD4), there are no active slip systems which can be distinguished. In this scribing direction, a perfect cleaving of the wafer along the (1−10) plane occurs.

As shown in FIG. 4A, except for the dicing in the [−1−12] direction, in all the rest of the dicing directions, several slip systems are active. These may create both edge chipping and sub surface dislocations during dicing in these directions. Furthermore, dicing experiments and device level testing revealed that the dicing direction SD2 can also produce good quality edges on both sides of the dicing direction. This may be because the slipping dislocations appear at a relatively shallow 30° angle to the diced edge which makes the affected area not very deep across the tile edges.

In one embodiment, the present inventors realized that by dicing the wafer 10 in a horizontal direction normal to the {110} major orientation flat, only one of the four side surfaces of each active detector tile 30 contains significant dicing damage. However, the other three side surfaces of the active detector tile 30 contain no or a small amount of dicing damage. Therefore, only one side of the active detector tile 30 may be polished to remove the dicing damage, while the other three side surfaces are not polished prior to placing each active detector tile 30 into an X-Ray detector.

Figure 4B:
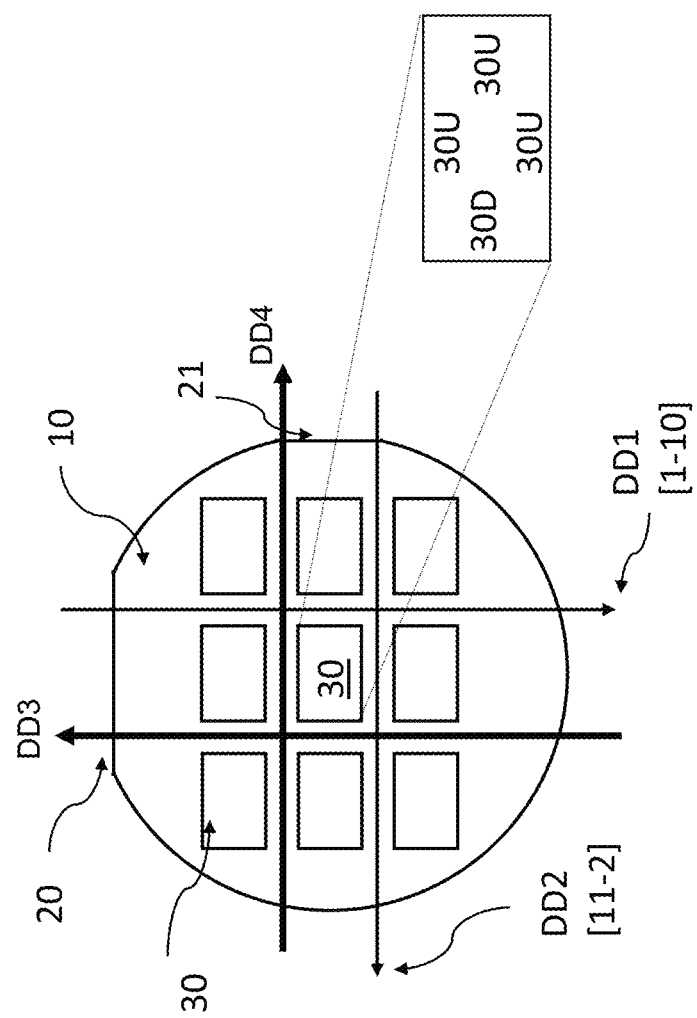
FIG. 4B is top view of a II-VI semiconductor wafer illustrating the dicing schematic aligned to the orientation flat according to one embodiment of the present disclosure.

FIG. 4B illustrates the dicing directions DD1, DD2, DD3 and DD4 for a single-crystal compound semiconductor wafer 10 having a zinc blende crystal structure with (111) surface, a Type I major orientation flat 20 comprising a {110} plane, such as the (−110) plane, and a minor orientation flat 21 comprising a {211} plane, such as the (−1−12) plane. The wafer 10 may comprise any suitable zinc blende compound semiconductor, such as CdTe or CZT.

The wafer 10 may be diced along first dicing directions which are within 3° of a line in one of the major surface normal to the major orientation flat 20. For example, the first dicing directions may be orthogonal to the major orientation flat 20 or may deviate from the orthogonal by 3° or less. In other words, the angle of dicing of the first dicing directions with respect to the normal to the major orientation flat 20 may be 3° or less, such as 0°. The first dicing directions may comprise the DD1 directions, the DD3 directions or both DD1 and DD3 directions in FIG. 4B.

The wafer 10 may then be diced along second dicing directions which are orthogonal to the first dicing directions to form a plurality of active detector tiles 30 having first and second major surfaces and four side surfaces. In other words, the angle of dicing of the second dicing directions with respect to the major orientation flat 20 itself may be 3° or less, such as 0°. The second directions may comprise the DD2 directions, the DD4 directions or both DD2 and DD4 directions. The dicing in the first and the second directions may be carried out in any order.

As shown in the inset of FIG. 4B, only one side surface 30D of each active detector tile 30 is damaged due to dicing. The other three side surfaces 30U are undamaged and contain no or a small amount of dicing damage. For example, if the wafer 10 comprises the Type I major orientation flat wafer, then the left side of the active detector tile 30 is the damaged surface 30D. Alternatively, if the wafer 10 comprises the Type II major orientation flat wafer, then the right side of the active detector tile 30 is the damaged surface 30D.

Thus, in this embodiment, only the one damaged side surface 30D of four side surfaces (30D, 30U) of the active detector tiles 30 is polished to remove the dicing damage. The other three side surfaces 30U may not be polished since they contain no or a low amount of dicing damage. Thus, the process complexity and cost are reduced by polishing only one of four side surfaces.

Figure 10:
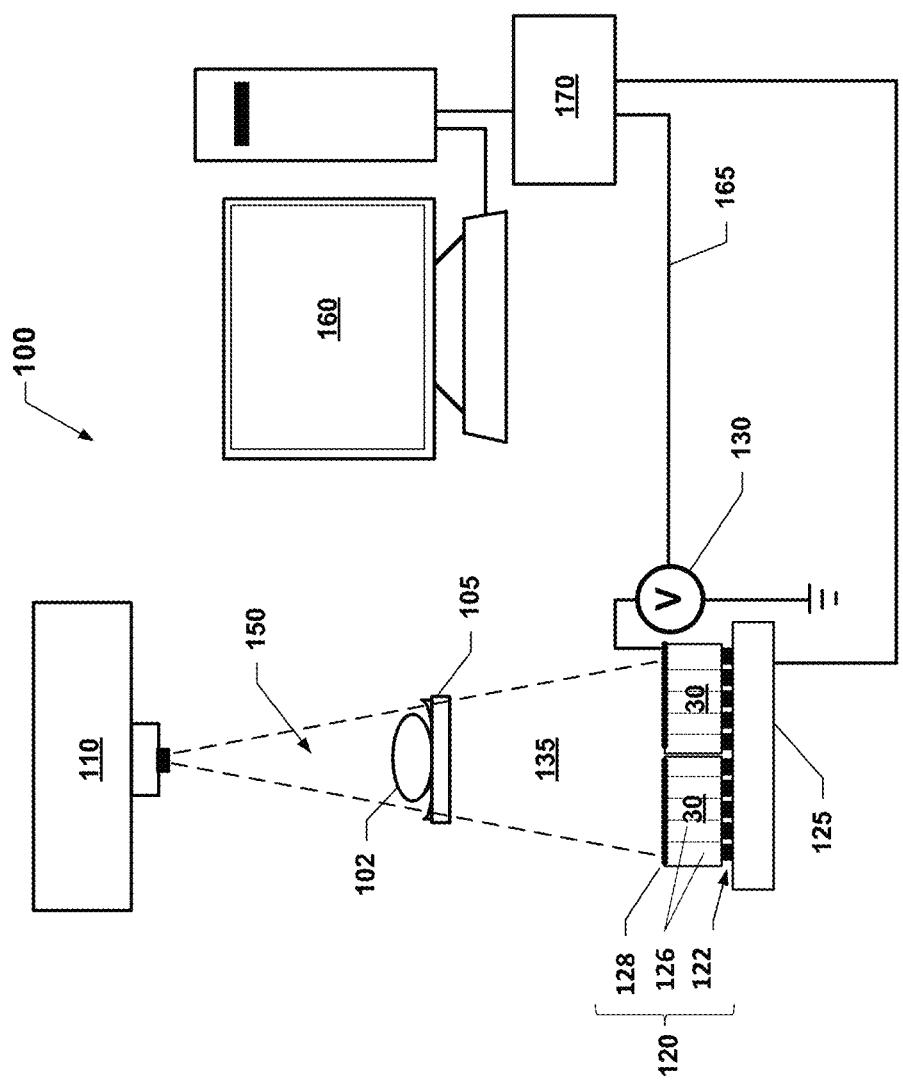
FIG. 10 is a block diagram of an X-ray imaging system suitable for use with the detector tiles of various embodiments of the present disclosure.

As shown in FIG. 10, after polishing only the damaged side surface 30D, at least one cathode 128 is formed on the first major surface of the radiation detector tiles 30 and at least one anode 122 is formed on the second major surface of the radiation detector tiles 30 after polishing only one damaged side surface 30D of four side surfaces of the active detector tiles without polishing other three side surfaces 30U of the active detector tiles.

In one embodiment, the first major surface of the radiation detector tiles 30 is the (−1−1−1) plane surface, and the second major surface of the radiation detector tiles is the (111) plane surface. The single-crystal compound semiconductor wafer 10 may comprise a cadmium zinc selenide wafer and the active detector tiles 30 may comprise cadmium zinc selenide tiles. The active detector tiles 30 may be placed into an X-ray radiation detector 120 (e.g., the detector located in a CT imaging system 100 shown in FIG. 10) without polishing the other three side surfaces.

In another embodiment, FIG. 5 illustrates the dicing directions DD5, DD6, DD7 and DD8 in which the edges of the detector tile 30 are rotated at an angle of 15° to the in-plane slipping [−110] and [−101] directions. The rotation schematic illustrated in the FIG. 5 is only one of the possibilities. Direction DD5 is rotated counter clockwise by an angle of 15° with respect to the [1−10] direction. Direction DD6 is rotated clockwise by an angle of 15° with respect to the [10−1] direction. Direction DD7 is rotated counter clockwise by an angle of 15° with respect to the [−110] direction. Direction DD8 is rotated clockwise by an angle of 15° with respect to the [−101] direction.

FIG. 6 is a schematic perspective view of a CdTe detector tile 30 obtained by dicing along directions DD5 to DD8 illustrated in FIG. 5. As shown in FIG. 6, the major (i.e., prominent) surface of the CdTe detector tile is a (111) plane and the side surface planes are rotated by 15° degrees counter clockwise to the (−110), (−1−12), (1−10) and (11−2) planes. Also illustrated in the FIG. 6 are the three slip planes (−111), (1−11) and (11−1) which are mutually oriented with each other and to the (111) wafer plane at 70.5°.

Figure 7:
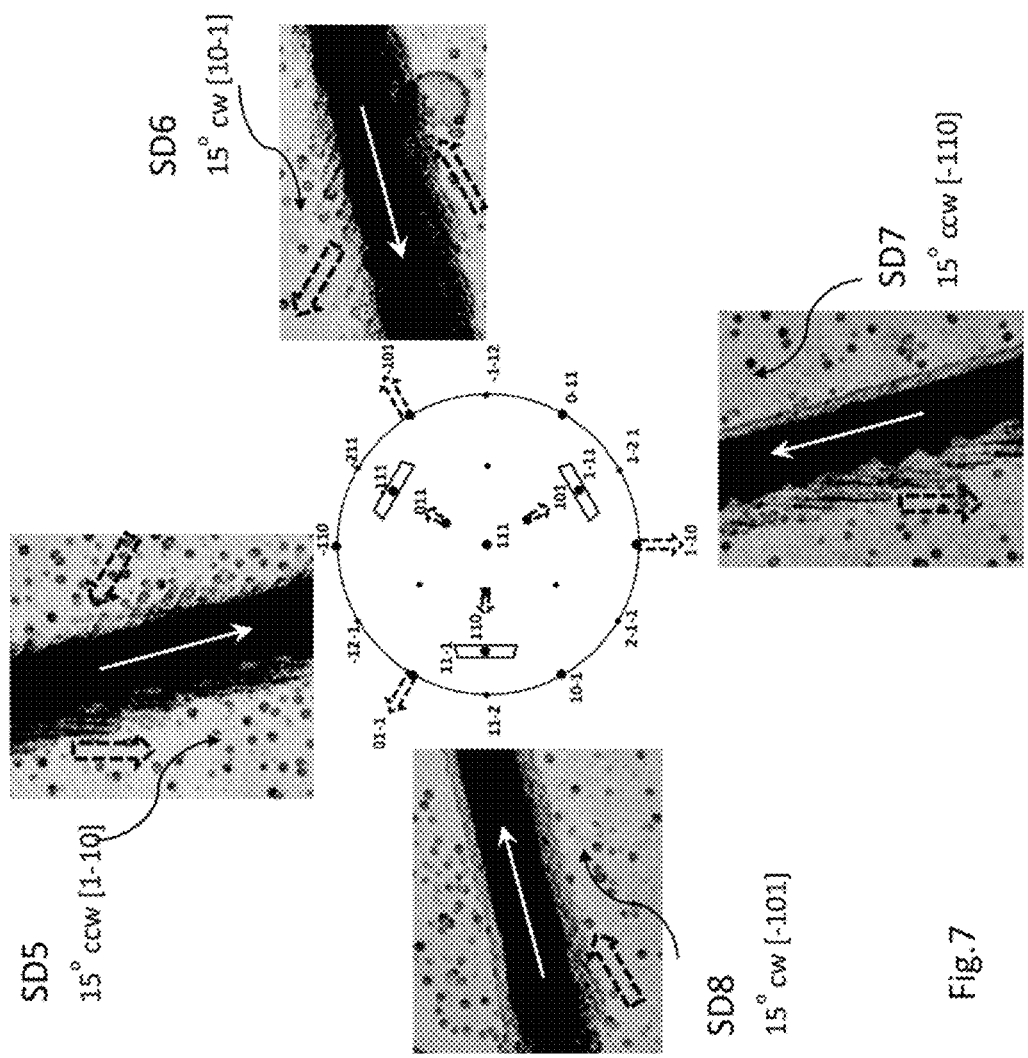
FIG. 7 shows micrographs of slip systems active during dicing of a (111) CZT wafer in directions rotated 15° to the in-plane slipping directions (e.g., rotated 15° to the orientation flat) relative to the schematic diagram of the stereographic projection shown in FIG. 1A. The slip systems are revealed by scribing in the illustrated directions and the dislocation pits highlighted by a Nakagawa etching solution.

The optical micrographs in the FIG. 7 illustrate the chipping and dislocation etch pits highlighted by the wet chemical etching of the scribed areas when scribed in the four directions SD5-SD8, 15° counter clockwise to [1−10], [11−2], [−110], & [−1−12] directions. The slip systems which are active in each of these scribing directions are marked with the dotted black colored arrows coinciding with the etch and chipping patterns. The white colored arrow in the middle of the scribed area indicates the direction of the scribe. The (111) pole figure is also presented together with the optical micrographs for ready visualization and correlation angles of the black arrows to the respective slip planes and slipping directions.

For the scribing direction SD5, which is rotated counter clockwise an angle of 15° to the [1−10] direction, the active slip systems are (11−1)/[1−10] at 15° to the right of scribing direction and (−111)/[01−1] at 45° to the left of scribing direction.

For the scribing direction SD6, which is rotated clockwise an angle of 15° to the [10−1] direction, the active slip systems are (1−11)/[−101] 15° to the left of scribing direction and (−111)/[01−1] at 45° to the right of scribing direction.

For the scribing direction SD7, which is rotated counter clockwise an angle of 15° to the [−110] direction, the active slip system is (11−1)/[1−10] at 15° to the left of scribing direction. There is no slip system active at the right side of the scribe.

For the scribing direction SD8, which is rotated clockwise an angle of 15° to the [−101] direction, the active slip system is (1−11)/[−101] at 15° to the right of scribing direction. There is no slip system active at the left side of the scribe.

It is further notable that all the active slip systems are in plane to the (111) wafer plane and there may be no active out of plane slip systems for these scribing directions. FIG. 7 also illustrates that when dicing or scribing are done in a direction 15° away from the slip direction in plane to the (111) wafer surface, the edge toward the slip direction has lesser or no defects. This gives a left-right anisotropy and directionality to the dicing. Furthermore, when dicing or scribing is done at an angle of 15° counter clockwise to the [−110] and [1−10] directions, higher quality edges are obtained on the right side edge of the tile 30. In contrast, when dicing or scribing is done at an angle of 15° clockwise to [−101] and [10−1] direction, the higher quality edges are obtained on the left side edge of the tile 30.

Without wishing to be bound by a particular theory, the present inventors believe that dicing energy/impulses causes cleaving and fracturing ahead of the dicing blade, such as a rotating dicing blade of a blade dicer apparatus. If the wafer is diced along the slip direction, then the cleaving may cause significant defects, especially to one side of the dicing blade. However, if the II-VI compound semiconductor wafer 10 having a zinc blende crystal structure is diced along a direction that is rotated (i.e., offset) by an angle of 13° to 17°, such as 14° to 16°, such as 15°, then as described above, the cleaving and fracturing defects in the diced tiles 30 may be reduced, especially on one side of the dicing blade. The offset angle depends on how close the top surface of the wafer is to the actual (111) plane, the dicing machine specifics and specific wafer material. A tape (e.g., UV releasable tape) and/or a sacrificial silicon wafer may be attached to the II-VI wafer 10 during dicing to further reduce the dicing damage.

Figure 8:
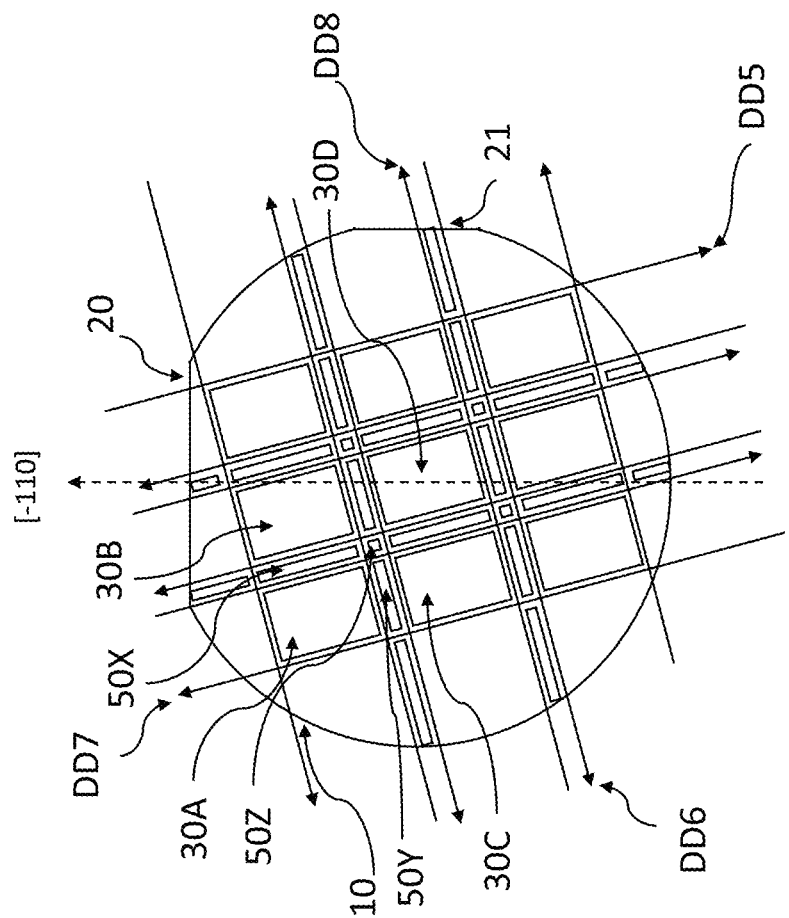
FIGS. 8 and 9 are top views of II-VI semiconductor wafers illustrating the bidirectional dicing schematic rotated 15° to the orientation flat which generate active and dummy (i.e., sacrificial) tiles according to alternative embodiments of the present disclosure.

FIG. 8 illustrates an alternative embodiment which includes bidirectional dicing which takes advantage of the left-right anisotropy and directionality of the dicing along a direction which is rotated (i.e., offset or misoriented) by an angle of 13° to 17° with respect to the <110> directions. In this embodiment, the wafer 10 is diced in two first opposite directions (i.e., directions which differ by 180°) between two detector tiles 30A and 30B of a first pair (30A, 30B) of adjacent active detector tiles, and then in two second opposite directions which are perpendicular to the two first directions between the first pair (30A, 30B) of adjacent detector tiles and a second pair (30C, 30D) of adjacent active detector tiles. Each of the four dicing directions is rotated (i.e., offset or misoriented) by an angle of 13° to 17° with respect to a respective <110> direction.

For example, referring to FIG. 8, the wafer 10 is diced in two first opposite directions DD5 and DD7 between two detector tile 30A and 30B of a first pair (30A, 30B) of adjacent active detector tiles, and then in two second opposite directions DD6 and DD8 which are perpendicular to the two first directions between the first pair (30A, 30B) of adjacent detector tiles and a second pair (30C, 30D) of adjacent active detector tiles.

Dummy tiles 50 may be present between the two dicing lines in the two first opposite directions DD5 and DD7, and between the two dicing lines in the two second opposite directions DD6 and DD8.

For example, a longer dummy tile 50X is present between the first pair (30A, 30B) of adjacent active detector tiles, and a shorter dummy tiles 50Y are present between the first pair (30A, 30B) and the second pair (30C, 30D) of adjacent active detector tiles (i.e., a shorter dummy tile 50Y is present between tiles 30A and 30C and another shorter dummy tile 50Y is present between tiles 30B and 30D). A smallest area dummy tile 50Z (having an area smaller than dummy tiles 50X and 50Y) is present between the four adjacent corners of the four active detector tiles 30A, 30B, 30C, 30D of the first and second pairs of adjacent active detector tiles.

The dummy tiles 50 may have a smaller area than the active detector tiles 30. The active detector tiles 30 have the four higher quality side edges, while the dummy tiles have the four lower quality side edges than the active detector tiles 30 based on each of the four dicing directions.

The dummy tiles 50 may not be used in a radiation detector, while the active detector tiles 30 are placed into a radiation detector, as will be described below with respect to FIG. 10 below. For example, the active detector tiles 30 may be used in a radiation detector in which at least two orthogonal sides, such as all four sides of each rectangular tile 30 are butted against an adjacent rectangular tile 30.

Figure 9:
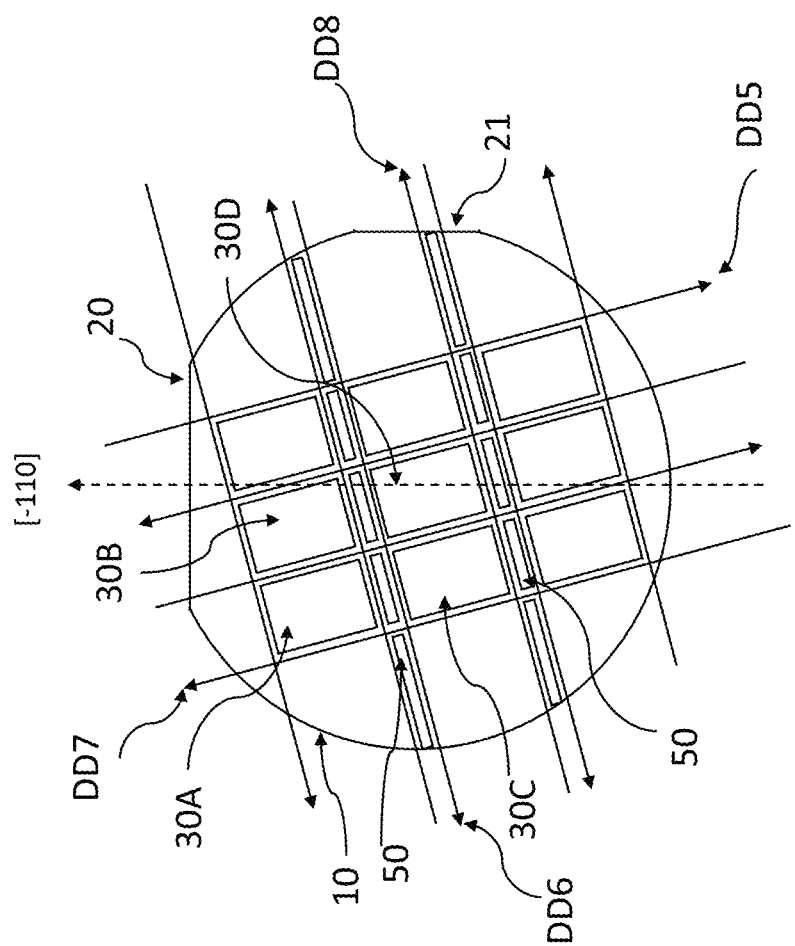

FIG. 9 illustrates another alternative embodiment which includes bidirectional dicing which takes advantage of the left-right anisotropy and directionality of the dicing along a direction which is rotated (i.e., offset or misoriented) by an angle of 13° to 17° with respect to the <110> directions. In this embodiment, the wafer 10 is diced in two first opposite directions (i.e., directions which differ by 180°) between two detector tiles 30A and 30B of a first pair (30A, 30B) of adjacent active detector tiles, as well as in one second direction which is perpendicular to the two first directions between the first pair (30A, 30B) of adjacent detector tiles and a second pair (30C, 30D) of adjacent active detector tiles.

For example, referring to FIG. 9, the wafer 10 is diced in two opposite directions DD6 and DD8 between two detector tile 30A and 30B of a first pair (30A, 30B) of adjacent active detector tiles, and in one of the two orthogonal directions DD5 or DD7 between the first pair (30A, 30B) of adjacent detector tiles and a second pair (30C, 30D) of adjacent active detector tiles. Dummy tiles 50 may be present between the two dicing lines in the two opposite directions DD6 and DD8, but not between the two dicing lines in the two orthogonal opposite directions DD5 and DD7.

The dummy tiles 50 may have a smaller area than the active detector tiles 30. The active detector tiles 30 have the two higher quality side edges, while the dummy tiles have the two lower quality side edges than the active detector tiles 30 based on each of the two opposite dicing directions.

The dummy tiles 50 may not be used in a radiation detector, while the active detector tiles 30 are placed into a radiation detector, as will be described below with respect to FIG. 10 below. For example, the active detector tiles 30 of this embodiment may be used in a linear radiation detector in which only two opposite sides of each rectangular tile 30 are butted against an adjacent rectangular tile 30.

Thus, in the embodiments of FIGS. 8 and 9, the dicing is conducted along directions which are misoriented by 13 to 17° with respect to the wafer flat 20 and the slip direction (e.g., a respective one of <110> directions) and with double pass dicing in opposite directions for one or both of the two orthogonal side surfaces of the active detector tiles 30. Thus, the edges of the active detector tiles 30 may always end up better (i.e., higher crystalline quality) than those of the sacrificial dummy tiles 50 located between the adjacent active detector tiles 30.

It should be noted that the method of the embodiments of the present disclosure is not only applicable to wafers. It can be applied to any object (e.g., substrate, etc.) as long as this object is single crystalline and has a zinc blende crystal structure.

FIG. 10 is a functional block diagram of an example ionizing radiation imaging system in accordance with various embodiments. The illustrated example ionizing radiation imaging system is a CT imaging system 100 that includes an X-ray source 110 (i.e., a source of ionizing radiation), and a radiation detector 120. The CT imaging system 100 may additionally include a support structure 105, such as a table or frame, which may rest on the floor and may support an object 102 to be scanned. The support structure 105 may be stationary (i.e., non-moving) or may be configured to move relative to other elements of the CT imaging system 100. The object 102 may be all or a portion of any biological (e.g., human patient) or non-biological (e.g., luggage) object to be scanned.

The X-ray source 110 is configured to deliver ionizing radiation to the radiation detector 120 by emitting an X-ray beam 135 toward the object 102 and the radiation detector 120. After the X-ray beam 135 is attenuated by the object 102, the beam of radiation 135 is received by the radiation detector 120. The radiation detector 120 includes at least two active detector tiles 30 of the embodiments of the present disclosure. Each active detector tile 30 includes at least one anode 122 and cathode 128 located on opposite sides of the active detector tile 30.

The radiation detector 120 may be controlled by a high voltage bias power supply 130 that selectively creates an electric field between an anode 122 and cathode 128 pair separated by the active detector tile 30. In one embodiment, each active detector tile 30 includes a plurality of separate CdTe or CZT pixels 126 (e.g., 4 to 1024, such as 256 to 864 pixels for example), each containing and electrically connected to a separate anode 122. One or more cathodes 128 are provided for the plurality of CZT pixels 126. A read-out application specific integrated circuit (ASIC) 125 coupled to the anode(s) 122 pair may receive signals (e.g., charge or current) from the anode(s) 122 and be configured to provide data to and by controlled by a control unit 170.

The control unit 170 may be configured to synchronize the X-ray source 110, the read-out ASIC 125, and the high voltage bias power supply 130. The control unit 170 may be coupled to and operated from a computing device 160. Alternatively, the computing device 160 and the control unit 170 may be integrated together as one device.

The object 102 may pass between the X-ray source 110 and the radiation detector 120 or alternatively the object may remain stationary while the X-ray source 110 and the radiation detector 120 move relative to the object 102. Either way, the radiation detector 120 may capture incremental cross-sectional profiles of the object 102. The data acquired by the radiation detector 120 may be passed along to the computing device 160 that may be located remotely from the radiation detector 120 via a connection 165. The connection 165 may be any type of wired or wireless connection. If the connection 165 is a wired connection, the connection 165 may include a slip ring electrical connection between any structure supporting the radiation detector 120 and a stationary support part of the support structure 105, which supports any part (e.g., a rotating ring). If the connection 165 is a wireless connection, the radiation detector 120 may contain any suitable wireless transceiver to communicate data with another wireless transceiver that is in communication with the computing device 160. The computing device 160 may include processing and imaging applications that analyze each profile obtained by the radiation detector 120, and a full set of profiles may be compiled to form two-dimensional images of cross-sectional slices of the object 102.

Various alternatives to the design of the CT imaging system 100 of FIG. 10 may be employed to practice embodiments of the present disclosure. CT imaging systems may be designed in various architectures and configurations. For example, a CT imaging system may have a helical architecture. In a helical CT imaging scanner, the X-ray source and detector array are attached to a freely rotating gantry. During a scan, a table (i.e., support structure 105) moves the object 102 smoothly through the scanner creating helical path traced out by the X-ray beam. Slip rings enable the transfer of power and data on and off the rotating gantry. In other embodiments, the CT imaging system may be a tomosynthesis CT imaging system. In a tomosynthesis CT scanner, the gantry may move in a limited rotation angle (e.g., between 15 degrees and 60 degrees) in order to detect a cross-sectional slice of the object. The tomosynthesis CT scanner may be able to acquire slices at different depths and with different thicknesses that may be constructed via image processing.

In one embodiment illustrated in FIGS. 6 and 7, a radiation detector tile 30 comprises a single crystal CdTe or its iso-valent alloy tile having a (111) plane first major (i.e., prominent) surface and four side surfaces which are rotated by an angle of 13° to 17° to a {110} family of planes.

In one embodiment, the tile 30 comprises single crystal cadmium zinc telluride. In one embodiment, the four side surfaces are rotated by an angle of 14° to 16° to the {110} family of planes. In another embodiment, the four side surfaces are rotated by an angle of 15° to the {110} family of planes. In the embodiment of FIG. 9, two first opposite side surfaces of the four side surfaces have a higher crystal quality than two second opposite side surfaces which are orthogonal to the two first opposite side surfaces.

In the embodiment of FIG. 10, a radiation detector 120 includes the radiation detector tile 30, at least one anode 122 located on a major surface of the radiation detector tile, and at least one cathode 128 located on another major surface of the radiation detector tile. In one embodiment, the radiation detector 120 comprises an X-ray radiation detector, the at least one cathode 128 is located on a (−1,−1,−1) plane major (i.e., prominent) surface of the radiation detector tile 30, the at least one anode 122 comprises a plurality of anodes located on the (111) plane major (i.e., prominent) surface of the radiation detector tile 30, the X-ray radiation detector 120 comprises a plurality of detector pixels 126, and each detector pixel 126 contains one anode of the plurality of anodes 122.

In the embodiment of FIG. 10, the X-ray imaging system 100 includes a plurality of X-ray radiation detectors 120, an X-ray source 110, a bias power supply 130, and a control unit (160, 170) configured to apply a voltage from the bias power supply to the plurality of X-ray radiation detectors 120.

In the embodiment of FIG. 5, a dicing method includes providing a single-crystal II-VI compound semiconductor material having a zinc blende crystal structure and having two surfaces which comprise (111) and (−1−1−1) planes, dicing the single-crystal II-VI compound semiconductor material along first dicing directions DD5 in a direction rotated by an angle of 13° to 17° to a {110} family of planes, dicing the single-crystal II-VI compound semiconductor material along second dicing directions DD7 which are opposite to the first dicing directions DD5, dicing the single-crystal II-VI compound semiconductor material along third dicing directions DD6 which are orthogonal to the first and the second dicing directions, and dicing the single-crystal II-VI compound semiconductor material along fourth dicing directions DD8 which are opposite to the third dicing directions DD6.

In one embodiment, the single-crystal II-VI compound semiconductor material comprises a single-crystal CdTe or its iso-valent alloy wafer 10, and the two surfaces comprise opposing major (i.e., prominent) surfaces which comprise the (111) and (−1−1−1) planes. In one embodiment, the single-crystal II-VI compound semiconductor material comprises a single-crystal cadmium zinc telluride wafer 10, the single-crystal cadmium zinc telluride wafer has a wafer flat 20 comprising a {110} plane, and dicing the single-crystal II-VI compound semiconductor material along the first dicing directions DD5 comprises dicing the single-crystal cadmium zinc telluride wafer 10 along the first directions rotated by the angle of 13° to 17° to the {110} plane of the wafer flat.

In one embodiment, dicing the single-crystal II-VI compound semiconductor material along the first dicing directions comprises dicing the single-crystal cadmium zinc telluride wafer 10 in the first directions DD5 rotated by an angle of 15° to the {110} family of planes, dicing the single-crystal II-VI compound semiconductor material along the second dicing directions comprises dicing the single-crystal cadmium zinc telluride wafer 10 in the second directions DD7 rotated by an angle of 15° to the {110} family of planes, dicing the single-crystal II-VI compound semiconductor material along the third dicing directions comprises dicing the single-crystal cadmium zinc telluride wafer in the third directions DD6 rotated by an angle of 15° to the {110} family of planes, and dicing the single-crystal II-VI compound semiconductor material along the fourth dicing directions comprises dicing the single-crystal cadmium zinc telluride wafer in the fourth directions DD8 rotated by an angle of 15° to the {110} family of planes to form a plurality of active detector tiles 30.

In the embodiment of FIG. 5, the first directions DD5 are rotated counter clockwise by an angle of 15° to a [1−10] direction of the single-crystal cadmium zinc telluride wafer 10, the second directions DD7 are rotated counter clockwise by an angle of 15° to a [−110] direction of the single-crystal cadmium zinc telluride wafer 10, the third directions DD6 are rotated clockwise by an angle of 15° to a [10−1] direction of the single-crystal cadmium zinc telluride wafer 10, and the fourth directions DD8 are rotated clockwise by an angle of 15° to a [−101] direction of the single-crystal cadmium zinc telluride wafer 10.

In the embodiments of FIGS. 8 and 9, a dicing method includes providing a single-crystal II-VI compound semiconductor wafer 10 having a zinc blende crystal structure, dicing the single-crystal II-VI compound semiconductor wafer along first dicing directions DD5, dicing the single-crystal II-VI compound semiconductor wafer along second dicing DD7 directions which are opposite to the first dicing directions DD5, dicing the single-crystal II-VI compound semiconductor wafer along third dicing directions DD6 which are orthogonal to the first and the second dicing directions, and dicing the single-crystal II-VI compound semiconductor wafer along fourth dicing directions DD8 which are opposite to the third dicing directions DD6 to form a plurality of active detector tiles 30. The II-VI compound semiconductor wafer 10 is diced in both the first direction DD5 and the second direction DD7 between two active detector tiles 30A and 30B of a first pair (30A, 30B) of adjacent active detector tiles to leave a first dummy tile 50 (e.g., 50X) between the two active detector tiles 30A and 30B of the first pair (30A, 30B) of adjacent active detector tiles. The first dummy tile 50 has a smaller area than each of the two active detector tiles 30A and 30B.

In the embodiment of FIG. 8, the II-VI compound semiconductor wafer 10 is diced in both the third direction DD6 and the fourth direction DD8 between the first pair (30A, 30B) of adjacent active detector tiles and a second pair (30C, 30D) of adjacent active detector tiles 30C and 30D to leave a second dummy tile 50Y between the first pair (30A, 30B) of adjacent active detector tiles and the second pair (30C, 30D) of adjacent active detector tiles. The second dummy tile 50Y has a smaller area than each of the active detector tiles 30A, 30B, 30C, or 30D of the first pair (30A, 30B) and the second pair (30C, 30D) of active detector tiles.

In one embodiment, the method also includes placing the active detector tiles 30 into a radiation detector 120 and not placing the dummy tile 50 into the radiation detector 120.

While the disclosure has been described in terms of specific embodiments, it is evident in view of the foregoing description that numerous alternatives, modifications and variations will be apparent to those skilled in the art. Each of the embodiments described herein may be implemented individually or in combination with any other embodiment unless expressly stated otherwise or clearly incompatible. Accordingly, the disclosure is intended to encompass all such alternatives, modifications and variations which fall within the scope and spirit of the disclosure and the following claims.

What is claimed is:

1. A radiation detector tile, comprising a single crystal compound semiconductor tile having a zinc blende crystal structure and having a (111) plane first major surface and four side surfaces which are rotated by an angle of 13° to 17° to a {110} family of planes.

2. The radiation detector tile of claim 1, wherein the tile comprises single crystal CdTe or its iso-valent alloy.

3. The radiation detector tile of claim 2, wherein the tile comprises single crystal cadmium zinc telluride.

4. The radiation detector tile of claim 1, wherein the four side surfaces are rotated by an angle of 14° to 16° to the {110} family of planes.

5. The radiation detector tile of claim 1, wherein the four side surfaces are rotated by an angle of 15° to the {110} family of planes.

6. A radiation detector, comprising:
the radiation detector tile of claim 1;
at least one anode located on a major surface of the radiation detector tile; and
at least one cathode located on another major surface of the radiation detector tile.

7. The radiation detector of claim 6, wherein:
the radiation detector comprises an X-ray radiation detector;
the at least one cathode is located on a (−1−1−1) plane major surface of the radiation detector tile;
the at least one anode comprises a plurality of anodes located on the (111) plane major surface of the radiation detector tile;
the X-ray radiation detector comprises a plurality of detector pixels; and
each detector pixel contains one anode of the plurality of anodes.

8. An X-ray imaging system, comprising:
a plurality of X-ray radiation detectors of claim 7;
an X-ray source;
a bias power supply; and
a control unit configured to apply a voltage from the bias power supply to the plurality of X-ray radiation detectors.

* * * * *